(12) United States Patent
Sakanishi

(10) Patent No.: US 8,012,923 B2
(45) Date of Patent: Sep. 6, 2011

(54) DETERGENT COMPOSITION

(75) Inventor: Yuichi Sakanishi, Ohtake (JP)

(73) Assignee: Daicel Chemical Industries, Ltd., Osaka-shi (JP)

( * ) Notice: Subject to any disclaimer, the term of this patent is extended or adjusted under 35 U.S.C. 154(b) by 57 days.

(21) Appl. No.: 12/503,224

(22) Filed: Jul. 15, 2009

(65) Prior Publication Data

US 2010/0016199 A1 Jan. 21, 2010

(30) Foreign Application Priority Data

Jul. 16, 2008 (JP) .................................. 2008-184612

(51) Int. Cl.
| | |
|---|---|
| C11D 17/08 | (2006.01) |
| C11D 17/00 | (2006.01) |
| A61K 8/00 | (2006.01) |
| A61Q 1/14 | (2006.01) |

(52) U.S. Cl. ........ 510/437; 510/130; 510/135; 510/136; 510/137; 510/158; 510/159; 510/404; 510/407; 510/417

(58) Field of Classification Search .................. 510/298, 510/130, 135, 136, 137, 158, 159, 404, 407, 510/417, 437
See application file for complete search history.

(56) References Cited

U.S. PATENT DOCUMENTS

| | | | | |
|---|---|---|---|---|
| 3,666,671 A | * | 5/1972 | Kalopissis et al. ............ | 510/119 |
| 4,788,345 A | * | 11/1988 | Sebag et al. ................. | 568/623 |
| 5,211,941 A | * | 5/1993 | Komori et al. .............. | 424/70.12 |
| 5,275,755 A | * | 1/1994 | Sebag et al. ................. | 510/121 |
| 5,961,994 A | * | 10/1999 | Cauwet et al. ................ | 424/401 |
| 6,210,693 B1 | * | 4/2001 | Inoue et al. ................... | 424/401 |
| 6,733,765 B2 | * | 5/2004 | Guillou et al. ................ | 424/401 |
| 2004/0197276 A1 | * | 10/2004 | Takase et al. .................. | 424/47 |
| 2005/0180942 A1 | * | 8/2005 | Shimizu et al. ............ | 424/70.31 |

FOREIGN PATENT DOCUMENTS

| | | | |
|---|---|---|---|
| EP | 1 438 946 A1 | | 7/2004 |
| EP | 1785410 A1 | * | 5/2007 |
| EP | 2 103 298 A1 | | 9/2009 |
| JP | 2004-75589 A | | 3/2004 |
| JP | 2005-336089 A | | 12/2005 |
| JP | 2005336089 A | * | 12/2005 |
| JP | 2006-282895 A | | 10/2006 |
| JP | 2006-347896 A | | 12/2006 |
| JP | 2008-94812 A | | 4/2008 |
| JP | 2009-67735 A | | 4/2009 |
| JP | 2009-073787 A | | 4/2009 |
| WO | WO-03/035015 A1 | | 5/2003 |
| WO | WO-2004/014334 A1 | | 2/2004 |

OTHER PUBLICATIONS

PDF of Derwent abstract of JP 2005336089 A, Dec. 2005, Nakajima et al.*
PDF of Machine translation of JP 2005336089 A, Dec. 2005, Nakajima et al.; machine translation obtained May 19, 2010.*
European Search Report dated Oct. 23, 2009 for European application No. 09165265.

* cited by examiner

Primary Examiner — Mark Eashoo
Assistant Examiner — Jane L Stanley
(74) Attorney, Agent, or Firm — Birch, Stewart, Kolasch & Birch, LLP

(57) ABSTRACT

A detergent composition contains a polyglycerol monoalkyl ether, water, a fat or oil, and a polyol. The polyglycerol monoalkyl ether is present in the composition at a content of 1 to 50 percent by weight based on the total amount of the composition. The detergent composition is useable as a foamable cleansing agent kind to the skin, exhibits superior detergency for oily cosmetics, and is usable even under wet conditions.

5 Claims, No Drawings

DETERGENT COMPOSITION

BACKGROUND OF THE INVENTION

1. Field of the Invention

The present invention relates to a detergent composition containing a polyglycerol monoalkyl ether, water, a fat or oil, and a polyol. The detergent composition is useful typically as a cleansing agent for oily cosmetics.

2. Description of the Related Art

Cleansing agents for cosmetics (makeups) are roughly classified mainly oil, gel, and foamable cleansing agents. Oil and gel cleansing agents generally require massaging by fingers so as to satisfactorily mix with cosmetics and to remove the cosmetics. A pressure is applied to the skin upon massaging, and this often damages the skin. In addition, these agents cause sticky feeling upon use and are not readily rinsable. In contrast, foamable cleansing agents are less irritating to the skin, excel in feel upon use, and have thereby been desirably used as cleansing agents.

Known foamable cleansing agents include those containing a foamable aerosol composition that is composed of an oil-in-water (O/W) emulsion including two phases, i.e., an inner phase and an aqueous phase. The inner phase is composed of an oily phase containing a propellant dissolved therein, and the aqueous phase has poor compatibility or miscibility with the propellant. However, cleansing agents using a foamable aerosol composition composed of an oil-in-water (O/W) emulsion are not appropriate as detergents for oily cosmetics, because they contain an aqueous phase as a continuous phase and thereby have poor miscibility with and poor detergency for oily cosmetics. Known foamable cleansing agents having improved detergency for oily cosmetics include water-in-oil (W/O) compositions for oily foamable aerosols, which contain a polyoxyethylene-added nonionic surfactant, an alkyl phosphate derivative, and a polyglycerol fatty acid ester, respectively (see Japanese Unexamined Patent Application Publication (JP-A) No. 2004-75589; PCT International Publication Number WO 2003/035015; and Japanese Unexamined Patent Application Publication (JP-A) No. 2006-347896). These water-in-oil (W/O) compositions for oily foamable aerosols, however, often suffer from phase transition from a water-in-oil (W/O) phase to an oil-in-water (O/W) phase upon cleansing of cosmetics and are difficult to use when used under wet conditions. Additionally, they have still insufficient detergency. Specifically, there has not yet been known a detergent composition which is useable as a foamable cleansing agent kind to the skin, exhibits superior detergency for oily cosmetics, and is usable even under wet conditions.

SUMMARY OF THE INVENTION

Accordingly, an object of the present invention is to provide a detergent composition which is usable as a foamable cleansing agent kind to the skin, exhibits superior detergency for oily cosmetics, and is usable even under wet conditions.

After intensive investigations, the present inventors have found that a detergent composition containing a polyglycerol monoalkyl ether in a specific amount, as well as water, a fat or oil, and a polyol can stably form fine and smooth foams and, if used as a cleansing agent for oily cosmetics, can sufficiently remove the oily cosmetics without placing a burden on the skin. They have also found that the detergent composition has superior solubility or miscibility both with an aqueous phase and with an oily phase, can thereby maintain a single-phase state within a wide range even where an aqueous phase and an oily phase are present as a mixture, can exhibit superior detergency even under wet conditions, and has good wash-up property. The present invention has been made based on these findings and further investigations.

Specifically, according to an embodiment of the present invention, there is provided a detergent composition containing a polyglycerol monoalkyl ether, water, a fat or oil, and a polyol, in which the polyglycerol monoalkyl ether is present at a content of 1 to 50 percent by weight based on the total amount of the composition.

The water is preferably present in the composition at a content of 1 to 50 percent by weight based on the total amount of the composition.

According to another embodiment of the present invention, there is provided a cleansing cosmetic which includes the detergent composition.

When the detergent composition according to the present invention is charged with a propellant into a tightly sealed container while being pressurized, a press of the spray button allows a mixture of the detergent composition and the propellant to be discharged at a single blow, and the propellant abruptly expands due to pressure reduction to thereby allow the detergent composition to form very fine foams.

The detergent composition according to the present invention contains a polyglycerol monoalkyl ether in a specific amount, as well as water, a fat or oil, and a polyol and can thereby stably form fine foams. The detergent composition, if used as a cleansing agent for oily cosmetics, can sufficiently remove the oily cosmetics without placing a burden on the skin, and shows good wash-up property. Additionally, the detergent composition has superior miscibility both with an aqueous phase and with an oily phase, can thereby maintain a single-phase state within a wide range even where an aqueous phase and an oily phase are present as a mixture, and can exhibit superior detergency even under wet conditions.

These and other objects, features, and advantages of the present invention will be understood more fully from the following description of the preferred embodiments. All numbers are herein assumed to be modified by the term "about."

DESCRIPTION OF THE PREFERRED EMBODIMENTS

A detergent composition according to an embodiment of the present invention contains a polyglycerol monoalkyl ether, water, a fat or oil, and a polyol, in which the polyglycerol monoalkyl ether is present at 1 to 50 percent by weight based on the total amount of the composition.

[Polyglycerol Monoalkyl Ether]

The polyglycerol monoalkyl ether is represented by following Formula (1):

wherein R represents an alkyl group; and "n" denotes an average number of repeating glycerol units and is 2 or more.

The repeating unit $C_3H_6O_2$ in the parentheses in Formula (1) may have both structures of following Formulae (2) and (3):

The symbol R represents an alkyl group. Exemplary alkyl groups include linear alkyl groups having about 1 to about 25 carbon atoms, such as methyl, ethyl, propyl, butyl, pentyl, hexyl, decyl, dodecyl, undecyl, lauryl, tridecyl, myristyl, pentadecyl, cetyl, heptadecyl, stearyl, and behenyl groups, of which those having about 10 to about 25 carbon atoms are preferred, and those having about 11 to about 22 carbon atoms are more preferred; and branched-chain alkyl groups having about 3 to about 25 carbon atoms, such as isopropyl, isobutyl, s-butyl, t-butyl, butyloctyl, isomyristyl, isocetyl, hexyldecyl, isostearyl, isobehenyl, octyldecyl, octyldodecyl, and isobehenyl groups, of which those having about 10 to about 25 carbon atoms are preferred, and those having about 11 to about 22 carbon atoms are more preferred.

Preferred alkyl groups as R include linear alkyl groups, of which more preferred are linear alkyl groups having about 10 to about 25 carbon atoms, such as decyl, dodecyl, undecyl, lauryl, tridecyl, myristyl, pentadecyl, cetyl, heptadecyl, stearyl, and behenyl groups.

The alkyl group may have one or more substituents. Exemplary substituents include halogen atoms, oxo group, hydroxyl group, substituted oxy groups (e.g., alkoxy groups, aryloxy groups, aralkyloxy groups, and acyloxy groups), carboxyl group, substituted oxycarbonyl groups (e.g., alkoxycarbonyl groups, aryloxycarbonyl groups, and aralkyloxycarbonyl groups), substituted or unsubstituted carbamoyl groups, cyano group, nitro group, substituted or unsubstituted amino groups, sulfo group, and heterocyclic groups. The hydroxyl group and carboxyl group may each be protected by a protecting group commonly used in organic syntheses.

The number "n" in Formula (1) denotes an average number of repeating glycerol units and is 2 or more, preferably 2 to 10, more preferably 2 to 5, and especially preferably 2 to 3. If the number "n" is 1, the resulting composition tends to have insufficient solubility in (miscibility with) water. In contrast, if the number "n" is excessively large, the composition tends to have excessively high solubility in water to thereby have insufficient solubility in oil.

Exemplary polyglycerol monoalkyl ethers for use herein include tetraglycerol monodecyl ether, tetraglycerol monododecyl ether, tetraglycerol monotetradecyl ether, triglycerol monodecyl ether, triglycerol monododecyl ether, triglycerol monotetradecyl ether, diglycerol monodecyl ether, diglycerol monododecyl ether, and diglycerol monotetradecyl ether. Among them, diglycerol monododecyl ether and diglycerol monotetradecyl ether are preferred. Each of different polyglycerol monoalkyl ethers can be used alone or in combination.

Such polyglycerol monoalkyl ethers for use herein can be prepared by any process not especially limited. Exemplary processes include a process of adding glycidol to an aliphatic alcohol in the presence of a basic catalyst, in which the glycidol is added in such a proportion that the ratio (by mole) of the aliphatic alcohol to glycidol be a specific ratio, and carrying out a reaction between them; a process of reacting an α-olefin epoxide with a polyglycerol; and a process of opening the ring of an alkyl glycidyl ether using a polyglycerol in the presence of an acid catalyst or a base catalyst.

The content of the polyglycerol monoalkyl ether is preferably from about 1.0 to about 50 percent by weight, and more preferably from about 10 to about 40 percent by weight, of the total amount of the composition, for satisfactory detergency and foam stability.

[Water]

Water for use herein can be either hard water or soft water. Exemplary waters include industrial water, tap water, ion-exchanged water, and distilled water. The content of water may be adjusted according to the purpose of use and is generally from about 1 to about 50 percent by weight, and preferably from about 20 to about 40 percent by weight, of the total amount of the composition.

[Fats and Oils]

Fats and oils for use herein can be any fats and oils that are in a liquid state during foaming and can be either natural fats and oils or synthetic fats and oils. The addition of such fats and oils enables stable formation of foams.

Exemplary fats and oils include liquid fats and oils such as avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, soybean oil, peanut oil, tea oil, kaya oil, rice bran oil, Chinese wood oil, Japanese wood oil (Japanese tung oil), jojoba oil, germ oil, glycerol trioctanoate, and glycerol triisopalmitate; hydrocarbons such as liquid paraffin, squalene, squalane, and pristane; higher fatty acids such as oleic acid, tall oil fatty acids, and isostearic acid; higher alcohols; silicones such as methylpolysiloxane, methylphenylpolysiloxane, methylhydrogenpolysiloxane, and decamethylpolysiloxane; esters such as isopropyl myristate, isopropyl palmitate, hexyl laurate, oleyl oleate, decyl oleate, octyldodecyl myristate, hexyldecyl dimethyloctanoate, diethyl phthalate, and dibutyl phthalate. Such fats and oils for use herein also include those obtained by subjecting the above fats and oils to a treatment such as hydrogenation or separation. The fat or oil may contain an unsaturated fatty acid, a sidechain fatty acid, a diglyceride, a monoglyceride, and other glyceride components, as long as the amount thereof is trivial.

The content of the fat or oil is, for example, from about 10 to about 99 percent by weight, and preferably from about 30 to about 95 percent by weight, of the total amount of the composition.

[Polyol]

The polyol component serves to destroy the liquid crystal structure of the polyglycerol monoalkyl ether, and the addition thereof helps the fat or oil component and water component to be dissolved in dramatically increased amounts. This helps to improve the feel upon use and foamability.

Exemplary polyols include glycerol, diglycerol, ethylene glycol, diethylene glycol, propylene glycol, polyethylene glycol, 1,3-butylene glycol, isoprene glycol, sorbitol, sorbitan, maltitol, trehalose, xylitol, glucose, erythritol, pentaerythritol, neopentyl glycol, sucrose, mannitol, gluconic acid, dipropylene glycol, hexylene glycol, and polyphenols.

Among them, glycerol, maltitol, 1,3-butylene glycol, propylene glycol, and sorbitol are preferably used alone or in combination in the present invention. These components can more satisfactorily destroy the liquid crystal structure and further improve the feel upon use and foamability.

The content of the polyol is, for example, from about 1 to about 40 percent by weight, and preferably from about 1 to about 25 percent by weight, of the total amount of the composition.

Where necessary, detergent compositions according to the present invention may further contain other components within ranges where the objects of the present invention can be achieved. Examples of such other components include nonionic surfactants other than the polyglycerol monoalkyl ethers; anionic surfactants; amphoteric surfactants; lower alcohols; powders; antioxidants; antioxidation assistants; ultraviolet-absorbers; humectants; antiphlogistic agents; preservatives; pH adjusters; extracts derived from animals, vegetables, fishes/shellfishes, and microorganisms; and flavors.

The nonionic surfactants other than the polyglycerol monoalkyl ethers are not especially limited, as long as being surfactants having no ionizable group as a hydrophilic group. Examples thereof include glycerol fatty acid esters, polyglycerol fatty acid esters, polyalkylene glycol fatty acid esters, sorbitan fatty acid esters, sugar fatty acid esters, pentaerythritol fatty acid esters, polyoxyalkylene hydrogenated castor oil fatty acid esters, fatty acid alkanolamides, polyoxyalkylene glycols, esters between a polyoxyalkylene glycol and a monohydric or polyhydric alcohol, polyoxyalkylene sugar ethers, condensates between a fatty amide and a polyoxyalkylene glycol, condensates between an aliphatic amine and a polyoxyalkylene glycol, and alkyl or alkenyl polyglycosides.

Exemplary anionic surfactants include, but are not specifically limited to, polyoxyethylene alkyl ether sulfate salts, alkyl sulfate salts, alkylbenzenesulfonate salts, α-olefinsulfonate salts, glutamic acid and other amino acid surfactants, N-acylmethyltaurate salts, and alkyl phosphate salts.

Exemplary amphoteric surfactants include, but are not specifically limited to, carboxybetaine-, imidazolinium-, sulfobetaine-, and alanine-type amphoteric surfactants.

Exemplary lower alcohols include, but are not specifically limited to, ethanol and propyl alcohol.

The powders (powdery components) are not especially limited and include inorganic powders and organic powders. Exemplary inorganic powders include talc, kaolin, mica, sericite, muscovite, phlogopite, synthetic mica, lepidolite, biotite, lithia mica, vermiculite, magnesium carbonate, zirconium silicate, aluminum silicate, barium silicate, calcium silicate, zinc silicate, magnesium silicate, strontium silicate, metal tungstates, magnesium, silica, zeolite, barium sulfate, calcined calcium sulfate (calcined gypsum), calcium phosphate, fluoroapatite, hydroxyapatite, ceramic powders, activated carbon, medical carbon (medical charcoal), metal soaps (e.g., zinc myristate, calcium palmitate, and aluminum stearate), and boron nitride. Exemplary organic powders include polyamide resin powders (nylon powders), polyethylene powders, poly(methyl methacrylate) powders, polystyrene powders, powders of styrene-acrylic acid copolymers, benzoguanamine resin powders, and cellulose powders.

Exemplary antioxidants include, but are not specifically limited to, vitamin E, dibutylhydroxytoluene, butylhydroxyanisole, and gallic acid esters.

Exemplary antioxidation assistants include, but are not specifically limited to, ascorbic acid, phytic acid, kephalin, and maleic acid.

Exemplary ultraviolet-absorbers include, but are not specifically limited to, benzophenone derivatives such as 2-hydroxy-4-methoxybenzophenone, 2-hydroxy-4-methoxybenzophenone-5-sulfonic acid, salts of 2-hydroxy-4-methoxybenzophenone-5-sulfonic acid, and dihydroxydimethoxybenzophenone; p-aminobenzoic acid and derivatives thereof such as ethyl p-aminobenzoate; methoxycinnamic acid derivatives such as ethyl p-methoxycinnamate, isopropyl p-methoxycinnamate, and octyl p-methoxycinnamate; salicylic acid derivatives such as octyl salicylate and phenyl salicylate; urocanic acid and derivatives thereof; 4-tert-butyl-4'-methoxydibenzoylmethane; 2-(hydroxy-5'-methylphenyl)benzotriazole; and methyl o-aminobenzoate (methyl anthranilate).

Exemplary humectants include, but are not specifically limited to, sodium lactate, pyrrolidonecarboxylic acid and derivatives thereof.

Exemplary antiphlogistic agents include, but are not specifically limited to, glycyrrhizic acid and derivatives thereof, glycyrrhetic acid and derivatives thereof, allantoin, hydrocortisone acetate, and azulene.

Exemplary preservatives include, but are not specifically limited to, methylparaben (methyl p-hydroxybenzoate), propylparaben(propyl p-hydroxybenzoate), and phenoxyethanol.

Exemplary pH adjusters include, but are not specifically limited to, citric acid, hydrochloric acid, sulfuric acid, phosphoric acid, sodium hydroxide, and ammonia.

Exemplary extracts derived from animals, vegetables (plants), fishes/shellfishes, and microorganisms include, but are not specifically limited to, extracts such as tea extract, aloe extract, ginkgo extract, swertia herb extract, mugwort extract, garlic extract, Scutellaria root extract, rosemary extract, sponge gourd extract, placental extract, extract from lactic acid bacteria culture, and seaweed extract.

Flavors for use herein are not specifically limited, as long as being those generally used in cosmetics.

When the detergent composition according to the present invention is charged together with a propellant into a hermetically sealed container while being pressurized, a press of the spray button allows a mixture of the detergent composition and the propellant to be discharged at a single blow, and the propellant abruptly expands due to pressure reduction to thereby allow the detergent composition to form very fine foams.

Exemplary propellants for use herein include chlorofluorocarbons such as trichlorofluoromethane, dichlorodifluoromethane, dichlorofluoromethane, trichlorotrifluoromethane, and dichlorotetrafluoromethane; liquefied gases such as propane, isobutane, isopentane, n-butane, and liquefied petroleum gas. Each of different propellants can be used alone or in combination. Each of these propellants may be used in combination with dimethyl ether, carbon dioxide gas, and/or nitrogen gas.

The content of the propellant is, for example, preferably from about 2 to about 90 percent by weight based on the total amount of the composition. A propellant, if its content is less than 2 percent by weight, may not sufficiently help to the composition to form satisfactory foams.

Detergent compositions according to the present invention are usable typically as detergents for oil stains, cleansing cosmetics for oily cosmetics, suntan oils, baby oils, hair oils, and foamy massage oils, and are advantageously usable as cleansing cosmetics typically for oily cosmetics.

EXAMPLES

The present invention will be illustrated in further detail with reference to several examples below. It should be noted, however, these examples are never intended to limit the scope of the present invention.

Examples 1 to 4 and Comparative Examples 1 to 4

Raw materials were mixed in proportions (by weight) given in Table 1, stirred and dissolved at 80° C., and the resulting solutions were cooled to ambient temperature (25° C.) and thereby yielded a series of detergent compositions.

Next, 18 g of each of the detergent compositions was charged into a 100-mL aerosol can, a valve was set thereto, and 2 g of liquefied petroleum gas as a propellant was charged thereinto, to give a series of aerosols. The resulting aerosols were tested and evaluated in the following manner.

[Foamability Test]

Each of the aerosols obtained in examples and comparative examples was sprayed for 2 seconds, the resulting foams were visually observed, and the foamability was evaluated according to the following criteria:

Criteria

Very uniform and fine foams were formed: A

Uniform and fine foams were formed: B

Coarse foams were formed: C

The sprayed aerosol did not form foams but remained as a liquid; D

[Foam Stability Test]

Each of the aerosols prepared in the examples and comparative examples was sprayed for 2 seconds, and the persistency of the resulting foams was evaluated according to the following criteria, in which the term "foam persisting time" refers to a time period within which the total volume of the foams decreased to 90% or less of the volume of foams immediately after spraying.

Criteria

The foam persisting time was 1 minute or longer: A

The foam persisting time was 30 seconds or longer but shorter than 1 minute: B

The foam persisting time was 10 seconds or longer but shorter than 30 seconds: C The sprayed aerosol did not form foams but remained as a liquid: D

[Detergency Test]

1. Detergency Test Under Dry Condition

A lipstick (trade name "Maquillage Superior Rouge RD759", supplied by Shiseido Co., Ltd.) (0.2 g) was applied to the forearm; about 0.5 g of each of the aerosol compositions prepared in the examples and comparative examples was taken in the hand and sufficiently mixed with the lipstick by massaging the applied portion thirty times. How the applied lipstick was removed after massaging was visually observed, and the detergency of the aerosol compositions was evaluated according to criteria mentioned below.

2. Detergency Test Under Water-Wetted Condition

A lipstick (trade name "Maquillage Superior Rouge RD759", supplied by Shiseido Co., Ltd.) (0.2 g) was applied to the forearm; the applied portion of the forearm was wetted with water; about 0.5 g of each of the aerosol compositions prepared in the examples and comparative examples was taken in the hand and sufficiently mixed with the lipstick by massaging the applied portion thirty times. How the applied lipstick was removed after massaging was visually observed, and the detergency of the aerosol compositions was evaluated according to the following criteria:

Criteria

The lipstick was completely removed: A

Almost all of the lipstick was removed: B

The lipstick slightly remained: C

Almost no lipstick was removed: D

TABLE 1

|  |  | Example | | | | Comparative Example | | | |
|---|---|---|---|---|---|---|---|---|---|
|  |  | 1 | 2 | 3 | 4 | 1 | 2 | 3 | 4 |
| Oil/fat | Olive oil | 59 | 59 | 59 | 59 | 80 | 80 | 80 | 80 |
|  | Water | 15 | 15 | 15 | 15 |  |  |  |  |
| Polyol | 1,3-Butylene glycol | 3 | 3 | 3 | 3 |  |  |  |  |
|  | Glycerol | 3 | 3 | 3 | 3 |  |  |  |  |

TABLE 1-continued

|  |  | Example | | | | Comparative Example | | | |
|---|---|---|---|---|---|---|---|---|---|
|  |  | 1 | 2 | 3 | 4 | 1 | 2 | 3 | 4 |
| Polyglycerol monoalkyl ether* | A | 20 |  |  |  | 20 |  |  |  |
|  | B |  | 20 |  |  |  | 20 |  |  |
|  | C |  |  | 20 |  |  |  | 20 |  |
|  | D |  |  |  | 20 |  |  |  | 20 |
| Foamability |  | A | A | A | A | B | C | B | B |
| Foam stability |  | B | A | A | B | C | C | B | C |
| Detergency | Dry condition | A | A | A | A | A | A | B | A |
|  | Wet condition | A | A | A | B | C | C | D | D |

*Polyglycerol monoalkyl ether A: Diglycerol monododecyl ether B: Triglycerol monododecyl ether C: Diglycerol monododecyl ether D: Triglycerol monotetradecyl ether While the above description is of the preferred embodiments of the present invention, it should be appreciated that the invention may be modified, altered, or varied without deviating from the scope and fair meaning of the following claims.

What is claimed is:

1. A detergent composition comprising a polyglycerol monoalkyl ether, water, a fat or oil, and a polyol, wherein the polyglycerol monoalkyl ether is present in the composition at a content of 20 to 50 percent by weight based on the total amount of the composition, and wherein the fat or oil is present in the composition at a content of 30 to 95 percent by weight based on the total amount of the composition.

2. The detergent composition according to claim 1, wherein the water is present in the composition at a content of 1 to 50 percent by weight based on the total amount of the composition.

3. A cleansing cosmetic, comprising the detergent composition of claim 1 or 2.

4. The detergent composition according to claim 1, wherein the polyglycerol monoalkyl ether is represented by following General Formula (1):

$$RO-(C_3H_6O_2)_n-H \qquad (1)$$

wherein R represents an alkyl group; "n" is 2 or more; and the unit $C_3H_6O_2$ has both structures of the following Formulae (2) and (3):

$$-CH_2-CHOH-CH_2O- \qquad (2)$$

$$CH(CH_2OH)CH_2O- \qquad (3).$$

5. The detergent composition according to claim 1, wherein the polyol is present in the composition at a content of 1 to 40 percent by weight of the total amount of the composition.

* * * * *